United States Patent [19]
Howbert et al.

[11] Patent Number: 5,302,724
[45] Date of Patent: Apr. 12, 1994

[54] ANTITUMOR COMPOSITIONS AND METHODS OF TREATMENT

[75] Inventors: J. Jeffry Howbert; Fariborz Mohamadi; Michael M. Spees, all of Indianapolis, Ind.

[73] Assignee: Eli Lilly and Company, Indianapolis, Ind.

[21] Appl. No.: 875,902

[22] Filed: Apr. 29, 1992

Related U.S. Application Data

[63] Continuation of Ser. No. 554,226, Jul. 17, 1990, abandoned.

[51] Int. Cl.$^5$ ............. C07D 209/04; C07D 209/52; C07D 209/16; C07D 209/36; C07D 207/12; C07D 207/24; C07D 207/30; C07D 209/02

[52] U.S. Cl. ................... 548/452; 548/469; 548/484; 548/486; 548/504; 548/506; 548/511; 548/512; 548/541; 548/543; 548/551; 548/560; 548/561; 548/570; 549/49; 549/74; 549/78; 549/434; 549/440; 549/462; 549/491; 564/32; 564/39; 564/47; 564/48; 564/53; 564/80; 564/90

[58] Field of Search ............. 548/452, 469, 484, 486, 548/504, 506, 511, 512, 541, 543, 551, 560, 561, 570; 549/49, 74, 78, 434, 440, 462, 491; 564/32, 39, 47, 48, 53, 80, 90

[56] References Cited

U.S. PATENT DOCUMENTS

| | | |
|---|---|---|
| 2,979,437 | 4/1961 | McLamore et al. . |
| 3,083,207 | 3/1963 | Hoehn et al. . |
| 3,097,241 | 7/1963 | Korger et al. . |
| 3,097,242 | 7/1963 | Hoehn et al. . |
| 3,102,115 | 8/1963 | Breuer et al. . |
| 3,102,121 | 8/1963 | Breuer et al. . |
| 3,124,597 | 3/1964 | Stoll et al. . |
| 3,155,721 | 11/1964 | Mills et al. . |
| 3,736,122 | 5/1973 | Tung et al. . |
| 3,849,110 | 11/1974 | Soper et al. . |
| 4,471,757 | 5/1978 | Levitt . |
| 4,620,868 | 11/1986 | Kimara et al. . |
| 4,845,128 | 7/1989 | Harper et al. . |
| 4,861,366 | 8/1989 | Levitt et al. . |

FOREIGN PATENT DOCUMENTS

| | | |
|---|---|---|
| 1208561 | 7/1986 | Canada . |
| 99339 | 7/1983 | European Pat. Off. . |
| 107214 | 9/1983 | European Pat. Off. . |
| 123303 | 4/1984 | European Pat. Off. . |
| 166615 | 1/1986 | European Pat. Off. . |
| 222475 | 9/1986 | European Pat. Off. . |
| 291269 | 5/1988 | European Pat. Off. . |
| 1240866 | 6/1961 | Fed. Rep. of Germany . |
| 1144259 | 2/1963 | Fed. Rep. of Germany . |
| 1159937 | 12/1963 | Fed. Rep. of Germany . |

OTHER PUBLICATIONS

Shawali et al. "Infrared spectroscopic study of 2-thiophenesulfonylurea and -thiourea derivatives" CA 81:62665b, 1974.

Abou Ouf et al. "Thiophenesulfonylureas structurally related to antidiabetic drugs" CA 84:17048d, 1976.

Holland, *J. Org. Chem.*, 26, 1662 (1961).

Shawali, et al., *Journal of Drug Research Egypt*, 5, (1), 117 (1973).

Derwent Abstract 86-95537/15.

Cassady et al., *J. Org. Chem.*, 23, 923 (1958).

Ruschig et al. in *Arzneimeit-Forsch.* 8, 448 (1958).

*Chemical Abstracts*, vol. 52, 17180i citing Haack et al., Ger. (East) 9688, Apr. 21, 1955.

F. Kurzer, *Chem. Rev.*, 50, 1 (1952).

Grindey et al., *Proceedings of the American Association for Cancer Research*, 27, Mar. 1986 (Abstract 1099).

Grindley et al., *Proceedings of the American Association for Cancer Research*, 28, 309 (1987) (Abstract No. 1224).

Houghton et al. in *Cancer Chemother Pharmacol* (1989), 25:84–88.

(List continued on next page.)

*Primary Examiner*—Nathan M. Nutter
*Attorney, Agent, or Firm*—Paul J. Gaylo; Leroy Whitaker; David E. Boone

[57] ABSTRACT

This invention provides certain sulfonamide compounds, formulations and method of use of certain sulfonamide compounds in treating susceptible neoplasms.

6 Claims, No Drawings

OTHER PUBLICATIONS

*Diabetes*, 19, iii–v (1970).

Derwent Abstract 85-200307/33 (1985). Japan Application J6-0126-219A.

S. Peterson, *Chem. Ber.*, 83, 551 (1950).

Hasegawa et al., *Chemical Society of Japan*, vol. 51, 1805 (1978).

Shah et al., *J. Med. Chem.*, 12, 938 (1969).

Lerner et al., *Metabolism*, 14, 578 (1965).

Breuer et al., *Chimie Therapeutique*, 659, Nov.–Dec. (1973).

Holland et al., *J. Med. Pharm. Chem.*, 3, (1), 99 (1961).

Chemical Abstract, 67, 54036t citing German 1240866 of Breuer, et al. (1967).

Chemical Abstract, 53, 20007h.

ANTITUMOR COMPOSITIONS AND METHODS OF TREATMENT

This application is a continuation of application Ser. No. 07/554,226, filed Jul. 17, 1990, now abandoned.

BACKGROUND OF THE INVENTION

According to the American Cancer Society about 494,000 people died from cancer in the United States in 1988. One of every five deaths from all causes in the United States is from cancer. Although chemotherapy has become one of the principal methods of treating cancer, the rate at which new drugs have become available for use in cancer chemotherapy has declined in recent years as reported by Horowitz et al. "Phase II Testing of Melphalan in Children with Newly Diagnosed Rhabdomyosarcoma: A Model for Anticancer Drug Development", *Journal of Clinical Oncology*, Vol. 6, No. 2, pp. 308–314 (1988). Accordingly, there is a substantial need for new drugs which are effective in inhibiting the growth of tumors.

To be particularly useful, a new chemotherapeutic agent should have a wide spectrum of activity, a large therapeutic index, and be chemically stable and compatible with other agents. Additionally, it would be beneficial for the new agent to have oral activity so that initial treatment and subsequent maintenance therapy is more convenient and less traumatic to the patient.

It has now been found that certain thiophenesulfonylureas are particularly useful in the treatment of solid tumors. These compounds are relatively nontoxic and provide an excellent therapeutic index.

Some diarylsulfonylureas have been reported as being active antitumor agents e.g., U.S. Pat. No. 4,845,128 of Harper et al. (1989), Grindey et al. *American Association of Cancer Research*, Vol. 27, pp 277 (1986) and Houghton et al., *Cancer Chemother. Pharmacol.*, (1989) 25, 84–88. There is no suggestion in these references of the thiophenesulfonylureas of the instant application or that these compounds would be useful as antitumor agents.

Certain thiophenesulfonylurea compounds have been reported. Shawali et al., *Journal of Drug Research Egypt*, Vol. 5, No. 1 pp. 117 (1973) reported N-thiophenesulfonyl-N'-(4-chlorobenzene)urea. Holland, *Journal of Organic Chemistry*, Vol. 26, pp. 1662 (1961) reported the preparation of several thiophenesulfonylurea compounds including certain N'-(4-fluorobenzene) compounds. McLamore, U.S. Pat. No. 2,979,437 (1961) discloses a number of arylalkenesulfonylureas as having hypoglycemic activity.

None of these references suggest or disclose the antitumor activity of the thiophenesulfonylurea compounds of the instant invention. Additionally, there is no suggestion or disclosure of the claimed compounds of the instant invention.

SUMMARY OF THE INVENTION

A method is provided for treating susceptible neoplasms in mammals which comprises administering to a mammal in need of such treatment an effective amount of a compound of the formula I

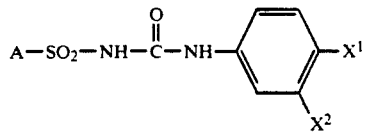

wherein:
$X^1$ and $X^2$ are independently hydrogen, halo, trifluoromethyl or methyl with the proviso that at least one of $X^1$ and $X^2$ is chlorine, bromine, fluorine, or trifluoromethyl;
A is

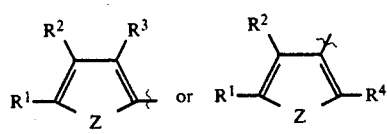

wherein
Z is oxygen, nitrogen or sulfur;
$R^1$, $R^2$, $R^3$ and $R^4$ are independently hydrogen, halo, $C_1$-$C_3$ alkyl, $C_1$-$C_3$ alkoxy, or $C_1$-$C_3$ alkylthio;
and pharmaceutically acceptable salts thereof In a further embodiment the instant invention comprises compounds of the formula I wherein:
$X^1$ and $X^2$ are independently hydrogen, halo, methyl or trifluoromethyl with the proviso that at least one of $X^1$ and $X^2$ is chlorine, bromine, fluorine, or trifluoromethyl;
A is

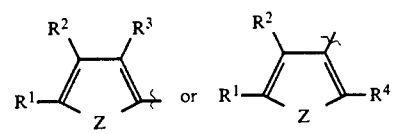

wherein:
Z is sulfur, oxygen or nitrogen;
$R^1$, $R^2$, $R^3$, and $R^4$ are independently hydrogen, $C_1$-$C_3$ alkyl, $C_1$-$C_3$ alkoxy, or $C_1$-$C_3$ alkylthio with the proviso that when A is

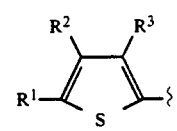

then at least one of $R^1$, $R^2$ or $R^3$ is a substituent other than hydrogen; and pharmaceutically acceptable salts thereof.

In another embodiment the present invention provides a method for treating susceptible neoplasms in mammals by administering to the mammal an effective amount of at least one compound of formula I.

In a further embodiment this invention provides pharmaceutical formulations comprising a compound of formula I in combination with a suitable pharmaceutical carrier, diluent or excipient. These formulations are particularly useful in treating mammals suffering from susceptible neoplasms.

DETAILED DESCRIPTION

As used herein the term "halo" refers to fluoro, chloro, bromo and iodo. The term "$C_1-C_3$ alkyl" refers to methyl, ethyl, n-propyl and isopropyl. The term "$C_1-C_3$ alkoxy" refers to methoxy, ethoxy, propoxy, and isopropoxy. The term "$C_1-C_3$ alkylthio" refers to methylthio, ethylthio, propylthio, and isopropylthio.

Preferred compounds for use in the instant method are those of formula I in which $X^1$ and $X^2$ are independently chloro, bromo, trifluoromethyl, or hydrogen with the proviso that at least one of $X^1$ and $X^2$ is chloro or bromo; Z is sulfur or oxygen; and $R^1$, $R^2$, $R^3$, and $R^4$ are independently hydrogen, $C_1-C_2$ alkyl, $C_1-C_2$ alkoxy, $C_1-C_2$ alkylthio, chloro, bromo, or fluoro.

Preferred compounds of the instant invention are those of formula I in which $X^1$ and $X^2$ are independently chloro, bromo, fluoro, trifluoromethyl and hydrogen with the proviso that at least one of $X^1$ and $X^2$ is chloro or bromo; Z is sulfur or oxygen; and $R^1$, $R^2$, $R^3$ and $R^4$ are independently hydrogen, $C_1-C_2$ alkyl, $C_1-C_2$ alkoxy, $C_1-C_2$ alkylthio, chloro, bromo or fluoro, with the proviso that when A is

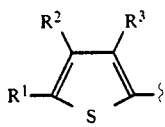

at least one of $R^1$, $R^2$ and $R^3$ is other than hydrogen.

More preferred compounds of formula I useful in the instant method include N-[[(4-chlorophenyl)amino]carbonyl]-4,5-dimethyl-2-thiophenesulfonamide; N-[[(3,4-dichlorophenyl)amino]carbonyl]-4,5-dimethyl2-thiophenesulfonamide; N-[[(4-chlorophenyl)amino]carbonyl]-2-thiophenesulfonamide; N-[[(4-chlorophenyl)amino]carbonyl]-5-(methylthio)-2-thiophenesulfonamide; N-[[(3,4-dichlorophenyl)amino]carbonyl]-2-thiophenesulfonamide; N-[[(3,4-dichlorophenyl)amino]carbonyl]5-methyl-2-thiophenesulfonamide; N-[[(4-chlorophenyl)amino]carbonyl]-5-propoxy-2-thiophensulfonamide; N-[[(3,4dichlorophenyl)amino]carbonyl]-5-ethyl-2-thiophenesulfonamide; N-[[(4-chlorophenyl)amino]carbonyl]-5-methyl-2-thiophenesulfonamide; and N-[[(4-chlorophenyl)amino]carbonyl]-3-methyl-2-thiophenesulfonamide, and salts thereof.

Most preferred compounds of the instant invention include N-[[(4-chlorophenyl)amino]carbonyl]5-chloro-2-thiophenesulfonamide; N-[[(4-chlorophenyl)amino]carbonyl]-5-ethyl-2-thiophenesulfonamide; N-[[(4-chlorophenyl)amino]carbonyl]-5-ethyl-2-furansulfonamide; N-[[(4-chlorophenyl)amino]carbonyl]-5-methoxy-2-thiophenesulfonamide; N-[[(4-chlorophenyl)amino]carbonyl]-5-ethoxy-2-thiophenesulfonamide, and salts thereof.

The compounds of formula I are generally referred to as derivatives of N-[[(substituted phenyl)amino]carbonyl]thiophenesulfonamides, -furansulfonamides or -pyrrolesulfonamides. Alternatively, the compounds can be referred to as 1- and 3-substituted sulfonylureas or N- and N'-substituted sulfonylureas.

This invention includes the pharmaceutically acceptable salts of the compounds of formula I. The compounds of this invention can react with basic materials such as alkali metal- or alkaline earth metal hydroxides, carbonates and bicarbonates, including without limitation sodium hydroxide, sodium carbonate, potassium hydroxide, calcium hydroxide, lithium hydroxide, etc. to form pharmaceutically acceptable salts such as the corresponding sodium, potassium, lithium or calcium salt. Nontoxic organic bases can also be used including primary, secondary and tertiary alkyl amines such as methylamine, triethylamine, and the like.

The compounds of formula I can be prepared by any of the methods known in the literature. Generally these methods involve either the reaction of a sulfonamide with an isocyanate or a reaction of a sulfonylcarbamate with an appropriately substituted aniline.

A preferred method of preparing the compounds of formula I involves the reaction of a sulfonamide of formula IIa or IIb

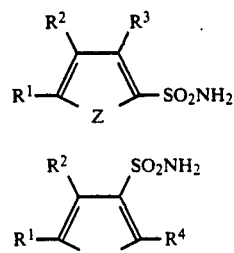

with a basic material to provide the reactive anion of formula II a' or IIb'

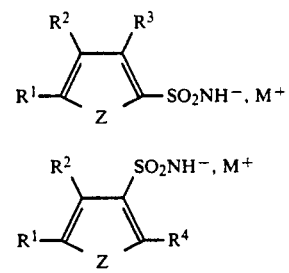

wherein $M^+$ is a counter ion, prior to contacting an arylisocyanate of formula III

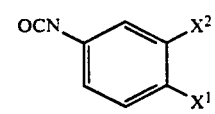

$X^1$, $X^2$, Z, $R^1$, $R^2$, $R^3$, and $R^4$ are the same as previously defined. Any suitable basic material can be used such as sodium hydroxide, potassium hydroxide, lithium hydroxide, sodium methoxide, sodium hydride and the like.

The reaction between anion IIa' or IIb' and III is usually performed using equal molar amounts of the two reactants although other ratios are operative. The reaction is preferably carried out in a solvent which is nonreactive under the reaction conditions such as benzene, toluene, acetonitrile, ethyl ether, tetrahydrofuran, dioxane, or most preferably acetone. The reaction can be carried out at temperatures from about 0° C. up to the boiling point of the reaction mixture. At the preferred temperature range of about 20° to 30° C., the reaction produces a strong exotherm and the reaction is usually complete within one hour. The product thus obtained is recovered by filtration and can be purified if desired by any number of methods known to those skilled in the art such as chromatography or crystallization.

The sulfonamide of formula IIa or IIb can be prepared by one of several methods depending upon the substituents which are on the heterocyclic ring. Generally, the more reactive heterocyclic materials which do not contain acid-sensitive substituents can be contacted with chlorosulfonic acid to provide the corresponding sulfonylchloride. This sulfonylchloride can then be reacted with ammonia or ammonium hydroxide to provide the corresponding sulfonamide. For materials which contain acid-sensitive substituents the lithium salt can be prepared by reaction with butyllithium followed by treatment with sulfur dioxide to provide the lithium sulfinate. Reaction of this sulfinate with N-chlorosuccinimide followed by ammonia/ammonium hydroxide or hydroxylamine-O-sulfonic acid and sodium acetate provides the sulfonamide. Less reactive heterocycles which do not have acid-sensitive substituents can be reacted with fuming sulfuric acid followed by neutralization with sodium carbonate to provide the sodium sulfonate salt. This salt can be conveniently converted to the sulfonylchloride by reaction with phosphorus oxychloride. The sulfonylchloride is subsequently reacted with ammonia or ammonium hydroxide to provide the sulfonamide component.

The starting materials and intermediates for the preparation of the present compounds are commercially available or can be readily prepared by the above-described methods or other methods known in the literature.

The following examples further illustrate the preparation of the compounds of this invention. The examples are provided for purposes of illustration only and are not to be construed as limiting the scope of the instant invention in any way.

The terms and abbreviations used in the instant examples have their normal meaning unless otherwise designed, for example, "THF" means tetrahydrofuran; "°C." refers to degrees celsius; "N" refers to normal or normality; "mmole" refers to millimole; "g" refers to gram; "ml" means milliliter; "M" refers to molar; "PMR" refers to proton magnetic resonance; and "m.s." refers to mass spectrometry.

EXAMPLE 1

A. 5-Ethyl-2-furansulfonamide

To a solution of 2-ethylfuran (3.7 g, 38.5 mmole) in 100 ml of anhydrous THF at −78° C. under nitrogen was added n-butyllithium (29.6 ml of 1.6M in hexanes, 38.5 mmole). This solution was stirred for 30 min. at 0° C. under nitrogen. Sulfur dioxide was bubbled through the flask for 20 min. and the reaction was concentrated under vacuum. To the resulting residue was added a solution of sodium acetate (24.9 g, 304 mmole) and hydroxylamine-0-sulfonic acid (11.3 g, 100 mmole) in 100 ml of water. This mixture was stirred at room temperature for 1.5 hrs. The reaction was added to water and extracted with methylene chloride. The combined organic layers were dried (sodium sulfate), filtered and concentrated under vacuum. The residue was passed through a plug of silica gel to provide 4.5 g of oil PMR (CD$_3$SOCD$_3$) 7.63 (s, 2H), 6.85 (d,J=4 Hz, 1H), 6.27 (d, J=4Hz, 1H), 2.70 (q, J=9 Hz, 2H) and 1.21 (t, J=9 Hz, 3H) ppm.

B. N-[[(4-chlorophenyl)amino]carbonyl]-5-ethyl-2-furansulfonamide

To a solution of 5-ethyl-2-furansulfonamide (4.5 g, 25.7 mmole) in 40 ml of acetone was added aqueous sodium hydroxide (25.7 ml of 1N, 25.7 mmole) followed by a solution of 4-chlorophenylisocyanate (3.9 g, 25.7 mmole) dissolved in 40 ml of acetone. The reaction was stirred at room temperature overnight and filtered through a plug of celite. The filtrate was acidified with hydrochloric acid (25.7 ml of 1N, 25.7 mmole) and the resulting precipitate filtered to produce 8.3 g of solid.

PMR (CD$_3$SOCD$_3$) 9.01 (s, 1H), 7.42 (d, J=9 Hz, 2H), 7.34 (d, J=9 Hz, 2H), 7.22 (d, J=4 Hz, 1H), 6.38 (d, J=4 Hz, 1H), 2.71 (q, J=9 Hz, 2H) and 1.20 (t, J=9 Hz, 3H) ppm.

Analysis for C$_{13}$H$_{13}$ClN$_2$O$_4$S:
Theory: C, 47.49; H, 3.99; N, 8.52.
Found : C, 47.48; H, 3.99; N, 8.48.

EXAMPLE 2

A. 2-Ethoxythiophene

2-Iodothiophene (59 g) and cupric oxide (11.2 g) were added to a solution of sodium ethoxide (from 19.7 g of sodium metal) in absolute ethanol (323 g). The mixture was stirred at reflux for 48 hr, filtered through celite, and cold water (1 L) was added. The mixture was extracted with ethyl ether which was then back extracted with a saturated aqueous sodium chloride solution, dried over MgSO$_4$, filtered and concentrated. The residue was then vacuum distilled at 50° C. and 10 torr pressure

B. 5-Ethoxy-N-[[(4-chlorophenyl)amino]carbonyl]-2-thiophenesulfonamide

To a solution of 4-chloroaniline (0.99 g, 7.8 mmole) in 30 ml of anhydrous THF at −78° C. under nitrogen was added chlorosulfonylisocyanate (1.09 g, 7.8 mmole). This mixture was stirred at −78° C. for 1 hr. 2-Ethoxythiophene (1 g, 7.8 mmole) was added, the ice bath was removed, and the reaction was stirred at room temperature for 2 hrs. The reaction was partially concentrated under vacuum, added to water and extracted with ethyl acetate. The organic layer was dried (sodium sulfate), filtered and concentrated under vacuum. The oil was chromatographed (4% methanol/methylene chloride) on silica gel. The desired fractions concentrated under vacuum and the resulting oil was dissolved in ethyl acetate (20 ml) and triturated with hexanes (450 ml) to provide 0.6 g of solid after drying under vacuum.

PMR (CD$_3$SOCD$_3$) 8.94 (s, 1H), 7.46 (d, J=9 Hz, 2H), 7.40 (d, J=6 Hz, 1H), 7.28 (d, J=9 Hz, 2H), 6 36 (d, J=6 Hz, 1H), 4.18 (q, J=9 Hz, 2H) and 1.36 (t, J=9 Hz, 3H) ppm.

Analysis for C$_{13}$H$_{13}$ClN$_2$O$_4$S$_2$:
Theory: C, 43.27; H, 3.63; N, 7.76.
Found : C, 42.99; H, 3.51; N, 7.69.

EXAMPLE 3

A. 5-Ethyl-2-thiophenesulfonamide

To a solution of chlorosulfonic acid (70 g, 600 mmole) in 1 L of chloroform at −5° to 0° C. was added (10 min) 2-ethylthiophene (25.0 g, 223 mmole) dissolved in 40 ml of chloroform. After the addition was completed, the reaction was stirred at 0° C. for 30 min The mixture was added to 500 ml of ice and poured into 1.5 L of water. The organic layer was separated and the aqueous layer extracted with 1 L of chloroform. The combined organic layers were concentrated under vacuum and the residue added to ammonium hydroxide (125 ml of conc. aqueous solution). This mixture was stirred at room temperature for 3 hrs. The solution was added to 500 ml of ice and acidified with hydrochloric acid (150 ml of conc. aqueous solution). This mixture was extracted with ethyl acetate/diethyl ether (2×400 ml, 1:1 volume). The combined organic layers were washed with water, dried (sodium sulfate) and filtered The solid was crystallized from ethyl acetate and hexanes (2:5 by volume) to provide 3.5 g of a tan solid. PMR (CD$_3$SOCD$_3$) 7.57 (s, 2H), 7.37 (d, J=6 Hz, 1H), 6.92 (d, J=6 Hz, 1H), 2.85 (q, J=9 Hz, 2H) and 1.26 (t, J=9 Hz, 3H) ppm.

B. N-[[(4-chlorophenyl)amino]carbonyl]-5-ethyl-2-thiophenesulfonamide sodium salt To a solution of 5-ethyl-2-thiophenesulfonamide (1.75 g, 9.16 mmole) in 20 ml of acetone was added aqueous sodium hydroxide (9.5 ml of 1N, 9.5 mmole) followed by a solution of 4-chlorophenyl isocyanate (1.4 g, 9.1 mmole) dissolved in 20 ml of acetone. The reaction was stirred at room temperature overnight and acidified with hydrochloric acid (10 ml of 1N, 10 mmole). The acetone was removed under vacuum and the solution extracted with diethyl ether (2×50 ml). The combined organic layers were dried (sodium sulfate), filtered and concentrated under vacuum. The oil was chromatographed (3% methanol/methylene chloride) on silica gel. The desired fractions concentrated and dissolved in methanol (20 ml) and sodium hydroxide (10 ml of 1N, 10 mmole). This solution was concentrated under vacuum and purified by reverse phase chromatography (20–60% acetonitrile/water gradient) using silica gel containing octadecyl groups (tradename "Rainin C-18 Dynamax-60A") to produce 0.74 g of solid.

PMR (CD$_3$SOCD$_3$) 8.68 (s, 1H), 7.52 (d, J=9 Hz, 2H), 7.24 (d, J=4 Hz, 1H), 7.14 (d, J=9 Hz, 2H), 6.68 (d, J=4 Hz, 1H), 2.76 (q, J=9 Hz, 2H) and 1.12 (t, J=9 Hz, 3H) ppm.

Analysis for C$_{13}$H$_{12}$ClN$_2$NaO$_3$S$_2$:
Theory: C, 43.57; H, 3.50; N, 7.64.
Found C, 43.36; H, 3.37; N, 7.52.

EXAMPLE 4

A. 5-Chloro-2-thiophenesulfonamide

5-Chloro-2-thiophenesulfonyl chloride (4 g, 18.4 mmole) was added to ammonium hydroxide (100 ml of conc. aqueous solution). This mixture was stirred at room temperature and concentrated under vacuum. The precipitate was filtered and washed with hexanes and water to produce 1.94 g of solid.

PMR (CD$_3$SOCD$_3$) 7.87 (s, 2H), 7.45 (d, J=4 Hz, 1H) and 7.23 (d, J=4 Hz, 1H) ppm.

B. 5-Chloro-N-[[(4-chlorophenyl)amino]carbonyl]-2-thiophenesulfonamide

To a solution of 5-chloro-2-thiophenesulfonamide 1.9 g, 10 mmole) in 10 ml of acetone was added aqueous sodium hydroxide (10 ml of 1N, 10 mmole) followed by a solution of 4-chlorophenyl isocyanate (1.54 g, 10 mmole) dissolved in 10 ml of acetone. This mixture was stirred at room temperature overnight. The reaction mixture was concentrated under vacuum and acidified with aqueous hydrochloric acid (10 ml of 1N, 10 mmole). The precipitate was filtered and the residue washed with hexanes and water. The solid was dried in a vacuum oven.

PMR (CD$_3$SOCD$_3$) 9.09 (s, 1H), 7.63 (d, J=4 Hz, 1H), 7.46 (d, J=9 Hz, 2H), 7.32 (d, J=9 Hz, 2H) and 7.24 (d, J=4 Hz 1H) ppm.

Analysis for C$_{11}$H$_8$Cl$_2$N$_2$O$_3$S$_2$:
Theory: C, 37.61; H, 2.29; N, 7.97.
Found : C, 38.07; H, 2.29; N, 7.72.

EXAMPLE 5

A. 5-Methoxy-2-thiophenesulfonamide

To a solution of 2-methoxythiophene (10 g, 87.7 mmole) in 400 ml of anhydrous tetrahydrofuran at −78° C. under nitrogen was added n-butyllithium (68.4 ml of 1.6M in hexanes, 109.6 mmole). This solution was stirred for 2 hrs. −78° C. under nitrogen. Sulfur dioxide was bubbled through the flask for 30 min. to produce a light yellow suspension. The reaction mixture was warmed to room temperature and was concentrated under vacuum. To the resuling residue was added a solution of sodium acetate (57.5 g, 701 mmole) and hydroxylamine-O-sulfonic acid (24.7 g, 219 mmole) in 350 ml of water. This mixture was stirred at room temperature for 1.5 hrs. The reaction was made basic (aq. sodium hydroxide) and extracted with diethyl ether. The aqueous layer was acidified (conc. hydrochloric acid) and extracted several times with methylene chloride The combined organic phases were washed with aqueous saturated sodium bicarbonate, dried (sodium sulfate) and concentrated under vacuum to provide 7.6 g of a light yellow solid.

PMR (CD$_3$SOCD$_3$) 7.48 (s, 2H), 7.22 (d, J=4 Hz, 1H), 6.34 (d, J=4 Hz, 1H) and 3.90 (s, 3H) ppm.

B. N-[[(4-chlorophenyl)amino]carbonyl]-5-methoxy-2-thiophenesulfonamide

To a solution of 5-methoxy-2-thiophenesulfonamide (7.6 g, 39.4 mmole) in 23 ml of acetone was added aqueous sodium hydroxide (46 ml of 1N, 46 mmole) followed by a solution of 4-chlorophenyl isocyanate (7.91 g, 51.3 mmole) dissolved in 23 ml of acetone. This mixture was stirred at room temperature for 18 hrs. and filtered. The filtrate was acidified with hydrochloric acid (47.5 ml of 1N, 47.5 mmole) and stirred vigorously for 30 min. The resultant precipitate was filtered and washed with water The material was slurried with a minimal amount of ethanol and filtered to produce 8.4 g of a colorless solid.

PMR (CD$_3$SOCD$_3$) 8.93 (s, 1H), 7.47 (d, J=4 Hz, 1H), 7.46 (d, J=9 Hz, 2H), 7.30 (d, J=9 Hz, 2H), 6.39 (d, J=4 Hz, 1H) and 3.95 (s, 3H) ppm.

Analysis for C$_{12}$H$_{11}$ClN$_2$O$_4$S$_2$:
Theory: C, 41.56; H, 3.20; N, 8.08.
Found : C, 41.83; H, 3.21; N, 8.32.

EXAMPLE 6

Preparation of N-[[(4-chlorophenyl)amino]carbonyl]-2-thiophenesulfonamide

The procedure of Example 4A was followed with thiophenesulfonylchloride (5 g) to provide 4.2 g of white solid, 2-thiophenesulfonamide.

The procedure of Example 4B was followed with 2-thiophenesulfonamide (4.2 g, 26 mmole) in 40 ml of acetone, 1N NaOH (26 ml, 26 mmole) and 4-chlorophenyl isocyanate (4.0 g, 26 mmole) in 40 ml of acetone. 7 g of named product were obtained PMR (CD$_3$SOCD$_3$) 10.88 (bs, 1H), 9.07 (s, 1H), 8.04 (d, J=4 Hz, 1H), 7.84 (d, J=4 Hz, 1H), 7.45 (d, J=9 Hz, 2H), 7.34 (d, J=9 Hz, 2H) and 7.23 (dd, J=4,4 Hz, 1H) ppm.

Analysis for C$_{11}$H$_9$ClN$_2$O$_3$S$_2$:
Theory: C, 41.71; H, 2.86; N, 8.84.
Found : C, 41.94; H, 2.92; N, 8.64.

EXAMPLE 7

Preparation of N-[[(3,4-dichlorophenyl)amino]carbonyl]-5-methyl-2-thiophenesulfonamide sodium salt The procedure of Example 3 was followed using 2-methylthiophene (8.0 g, 81.6 mmole), chlorosulfonic acid (28.4 g, 245 mmole) and 200 ml concentrated ammonium hydroxide to produce 5-methyl-2-thiophenesulfonamide which was contacted with 3,4-dichlorophenyl isocyanate (2.61 g, 13.8 mmole) and 1N NaOH (14.5 ml) in 10 ml acetone to provide 3.5 g of the named product as a solid.

PMR (CD$_3$SOCD$_3$) 8.92 (s, 1H), 7.94 (d, J=3 Hz, 1H), 7.34 (d, J=3 Hz, 1H), 7.33 (s, 1H), 7.22 (d, J=6 Hz, 1H), 6.68 (d, J=6 Hz, 1H) and 2.42 (s, 3H) ppm.

Analysis for C$_{12}$H$_9$Cl$_2$N$_2$NaO$_3$S$_2$:
Theory: C, 37.22; H, 2.34; N, 7.23.
Found : C, 37.52; H, 2.61; N, 7.07.

EXAMPLE 8

Preparation of N-[[(4-chlorophenyl)amino]carbonyl]-5-(methylthio)-2-thiophenesulfonamide The procedure of Example 5 was followed with 2-thiomethylthiophene (2.0 g, 15.2 mmole) in anhydrous THF (50 ml) and 1.6M n-butyllithium (9.5 ml, 15.2 mmole) with SO$_2$ gas for 15 minutes. A solution of sodium acetate (9.8 g, 120 mmole) and hydroxylamine-O-sulfonic acid (4.5 g, 39.4 mmole) in 50 ml of water was added. The resulting sulfonamide (1.5 g, 7.2 mmole) was contacted with 1N NaOH (7.2 ml, 7.2 mmole) and 4-chlorophenyl isocyanate (1.1 g, 7.2 mmole) in 10 ml of acetone to provide the named product (2.2 g).

PMR (CD$_3$SOCD$_3$) 9.18 (s, 1H), 7.69 (d, J=4 Hz, 1H), 7.44 (d, J=9 Hz, 2H), 7.35 (d, J=9 Hz, 2H), 7.13 (d, J=4 Hz, 1H) and 2.64 (s, 3H) ppm.

Analysis for C$_{12}$H$_{11}$ClN$_2$O$_3$S$_3$:
Theory: C, 39.72; H, 3.06; N, 7.72.
Found : C, 39.44; H, 3.07; N, 7.58.

EXAMPLE 9

Preparation of 5-ethyl-N-[[(3,4-dichlorophenyl)amino]carbonyl]-2-thiophenesulfonamide sodium salt The procedure of Example 3B was followed with 5-ethyl-2-thiophenesulfonamide (2.0 g, 10.5 mmole), 1N NaOH (10.5 ml) and 3,4-dichlorophenyl isocyanate (1.97 g, 10.5 mmole) in 10 ml acetone to provide the named product (2.77 g).

PMR (CD$_3$SOCD$_3$) 8.94 (s, 1H), 7.98 (s, 1H), 7.38 (m, 2H), 7.26 (d, J=4 Hz, 1H), 6.72 (d, J=4 Hz, 1H), 2.78 (q, J=9 Hz, 2H) and 1.22 (t, J=9 Hz, 3H) ppm.

Analysis for C$_{13}$H$_{11}$Cl$_2$N$_2$NaO$_3$S$_2$:
Theory: C, 38.91; H, 2.76; N, 6.98.
Found : C, 38.66; H, 2.62; N, 6.68.

EXAMPLE 10

Preparation of N-[[(4-chlorophenyl)amino]carbonyl]-5-propoxy-2-thiophenesulfonamide

A. Preparation of 2-propoxythiophene

Iodothiophene (59 g, 281 mmole) and cupric oxide (11.2 g, 141 mmole) were placed in propanol (420 g) containing sodium (19.7 g, 857 mmole). The mixture was stirred at reflux for 48 hours and then filtered. The filtrate was added to cold water and the water extracted with ethyl ether. The ether layers were combined, dried over magnesium sulfate, filtered, concentrated, and then vacuum distilled from over sodium at 50° C. and 10 torr to provide 5.4 g of product.

B. Preparation of 5-propoxy-2-thiophenesulfonamide

The procedure of Example 5A was followed using the product thiophene (2.0 g, 15.2 mmoles) from 10A above, anhydrous THF (80 ml), 1.6N n-butyllithium (9.5 ml, 15.2 mmole) and SO$_2$ gas for 15 minutes Sodium acetate (9.8 g, 120 mmole) and hydroxylamine-O-sulfonic acid (4.5 g, 39.4 mmole) in water (50 ml) provided product (1.3 g).

C. Preparation of N-[[(4-chlorophenyl)amino]carbonyl]-5-propoxy-2-thiophenesulfonamide The procedure of Example 5B was followed using the product (1.3 g, 6.2 mmole) from Example 10B, 1N NaOH (6.2 ml, 6.2 mmole), acetone (15 ml), 4-chlorophenyl isocyanate (950 mg, 6.2 mmole) in acetone (10 ml). After stirring overnight at room temperature, the mixture was filtered and 1N HCl (6.2 ml, 6.2 mmole) was added. Workup provided the named product as a white powder (1.4 g).

PMR (CD$_3$SOCD$_3$) 10.66 (bs, 1H), 8.99 (s, 1H), 7.54 (d, J=4 Hz, 1H), 7.44 (d, J=9 Hz, 2H), 7.35 (d, J=9 Hz, 2H), 6.44 (d, J=4 Hz, 1H), 4.11 (t, J=8 Hz, 2H), 1.76 (sext, J=8 Hz, 2H) and 0.96 (t, J=8 Hz, 3H) ppm.

Analysis for C$_{14}$H$_{15}$ClN$_2$O$_4$S$_2$:
Theory: C, 44.86; H, 4.03; N, 7.47.
Found : C, 45.14; H, 4.04; N, 7.52.

EXAMPLE 11

Preparation of N-[[(4-chlorophenyl)amino]carbonyl]-5-methyl-2-thiophenesulfonamide

A. Preparation of 5-methyl-2-thiophenesulfonamide

2-Methylthiophene (9.8 g, 0.1 mole) was dissolved in dry THF (75 ml) under nitrogen. n-Butyl lithium (62.5 ml, 0.1 mole) was added over a five minute period by a syringe while the mixture was maintained at −40° C. The mixture was then warmed to between −20° and −30° C. and maintained for one hour. SO$_2$Cl$_2$ (27 g, 0.2 mole) in 50 ml of hexane was cooled to −30° C. and the n-butyl lithium solution was added while maintaining the temperature at −20° C. to −30° C. The mixture was stirred overnight at room temperature and then water (75 ml) was added while cooling the mixture in an ice bath. The organic layer was separated and passed through Na$_2$SO$_4$. After removing solvent by evaporation, the resulting yellow-orange oil was added to concentrated NH₄OH (100 ml) and the mixture was then warmed to 60° C. The resulting solid was collected by filtration and recrystallized from toluene to provide 1.3 g of product after drying under vacuum at 60° C.

PMR: 270MHz (DMSO) 2.48 (s, 3 H), 6.83 (d, J=6 Hz, 1 H), 7.34 (d, J=6 Hz, 1 H), 7.56 (br s, 2 H) ppm.

Analysis for $C_5H_7NO_2S_2$:
Theory: C, 33.88; H, 3.98; N, 7.90.
Found: C, 34.13; H, 3.94; N, 7.67.

B. Preparation of N-[[(4-chlorophenyl)amino]carbonyl]-5-methyl-2-thiophenesulfonamide 5-Methyl-2-thiophenesulfonamide (0.97 g, 5.5 mmole) was dissolved in acetone (3 ml) and NaOH (1N, 5.8 ml, 5.8 mmole) was added. The solution was stirred for 15 minutes and then 4-chlorophenyl isocyanate (0.94 g, 6.1 mmole) dissolved in acetone (3 ml) was added dropwise to the sulfonamide solution. The mixture was stirred at room temperature overnight, filtered and the filtrate acidified with HCl (1N, 5.8 ml). The mixture was diluted with water (30 ml) and stirred at room temperature overnight. Solid was collected by filtration, washed with water and dried under vacuum at 60° C. to provide 1.68 g of product.

PMR: 270MHz (DMSO) 2.52 (s, 3H), 6.92 (d, J=6 Hz, 1 H), 7.34 (d, J=9 Hz, 2 H), 7.42 (d, J=9 Hz, 2H), 7.62 (d, J=6 Hz, 1 H), 9.01 (s, 1 H), c. 10.0 (v br s, 1 H). m.s.=330 (M+).

Analysis for $C_{12}H_{11}N_2O_3S_2Cl$:
Theory: C, 43.57; H, 3.35; N, 8.47; S, 19.39.
Found: C, 43.46; H, 3.21; N, 8.42; S, 19.57.

EXAMPLE 12

Preparation of 3-methyl-N-[[(4-chlorophenyl)amino]carbonyl]-2-thiophenesulfonamide The procedure of Example 3A was followed with 3-methylthiophene (10.0 g, 102 mmole), chlorosulfonic acid (29.58 g, 255 mmoles) in chloroform (200 ml), concentrated ammonium hydroxide, to provide 3-methyl-2-thiophenesulfonamide.

The procedure of Example 4B was followed with the 3-methyl-2-thiophenesulfonamide (1.6 g, 9.0 mmole), 1N NaOH (9.0 ml), acetone (10 ml), 4-chlorophenyl isocyanate (1.4 g, 9.2 mmole), 1N HCl (9.5 ml) to provide the named product (1.7 g).

PMR (CD₃SOCD₃) 8.86 (s, 1H), 7.88 (d, J=6 Hz, 1H), 7.40 (d, J=9 Hz, 2H), 7.32 (d, J=9 Hz, 2H), 7.06 (d, J=6 Hz, 1H) and 2.48 (s, 3H) ppm.

Analysis for $C_{12}H_{11}ClN_2O_3S_2$:
Theory: C, 43.57; H, 3.35; N, 8.47.
Found : C, 43.80; H, 3.30; N, 8.66.

EXAMPLE 13

Preparation of 4,5-dibromo-N-[[(4-chlorophenyl)amino]carbonyl]-2-thiophenesulfonamide The procedure of Example 4 was used with 4,5-dibromo-2-thiophenesulfonylchloride (in excess of 3 g) in THF with concentrated ammonium hydroxide to provide the corresponding sulfonamide as solid product (3.1 g). This sulfonamide (3.1 g, 9.6 mmole) in acetone (20 ml) was combined with 55% NaH in oil (418 mg, 9.6 mmole), 4-chlorophenyl isocyanate (1.5 g, 9.6 mmole) in acetone (15 ml), then 1N HCl (9.6 ml, 9.6 mmole) to provide the named product (about 3 g).

PMR (CD₃SOCD₃) 9.26 (s, 1H), 7.80 (s, 1H), 7.45 (d, J=9 Hz, 2H) and 7.35 (d, J=9 Hz, 2H) ppm Analysis for $C_{11}H_7Br_2ClN_2O_3S_2$:
Theory: C, 27.84; H, 1.49; N, 5.9.
Found C, 28.05; H, 1.48; N, 5.76.

EXAMPLE 14

Preparation of N-[[(4-chlorophenyl)amino]carbonyl]-4,5-dimethyl-2-thiophenesulfonamide The procedure of Example 3A was followed with 2,3-dimethylthiophene (6.0 g, 53.6 mmole), chlorosulfonic acid (27.5 g), dry chloroform (160 ml total), and concentrated ammonium hydroxide to provide solid 4,5-dimethyl-2-thiophenesulfonamide. The sulfonamide (1.5 g, 7.7 mmole), 1N NaOH (7.7 ml), acetone (7.0 ml) were combined and 4-chlorophenyl isocyanate (1.14 g, 7.7 mmole), 1N HCl (7.7 ml) to provide the named product (1.0 g).

PMR (CD₃SOCD₃) 8.82 (s, 1H), 7.46 (d, J=9 Hz, 2H), 7.43 (s, 1H), 7.28 (d, J=9 Hz, 2H), 2.34 (s, 3H) and 2.10 (s, 3H) ppm.

Analysis for $C_{13}H_{13}ClN_2O_3S_2$:
Theory: C, 45.28; H, 3.80; N, 8.12.
Found : C, 45.05; H, 3.66; N, 7.96.

EXAMPLE 15

Preparation of 5-propyl-N-[[(4-chlorophenyl)amino]carbonyl]-2-thiophenesulfonamide sodium salt A. Preparation of 2-(n-propyl)thiophene Ethylene glycol (150 ml) and potassium hydroxide (25 g as 85% aqueous solution) were combined and heated to about 80° C. to dissolve the potassium hydroxide. Hydrazine (15 ml) was added followed by 1-(2-thienyl)-1-propanone (15 g, 107 mmole) The mixture was heated to reflux at about 200° C. for three hours. Additional ethylene glycol was added and product was collected in a Dean Stark trap. The ethylene glycol layer was separated from the product layer which was a yellow liquid. The product liquid was distilled in vacuo (about 5 mm Hg) at 35°-37° C. to provide 2-(n-propyl)thiophene (7.45 g).

PMR (CDCl₃) 7.1 (d, J=5 Hz, 1H), 6.9 (t, J=3,5 Hz, 1H), 6.8 (d, 3 Hz, 1H), 2.8 (t, J=10 Hz, 2H), 1.7 (m, 2H), 1.0 (t, J=9 Hz, 3H ).

m.s.=126 parent ion.

B. Preparation of 5-(n-propyl)-2-thiophenesulfonamide

The procedure of Example 3A was followed with the thiophene from Example 15A (5.0 g, 39.7 mmole), chlorosulfonic acid (13.83 g, 7.89 ml, 119.1 mmole), chloroform (150 ml), concentrated ammonium hydroxide (80 ml), concentrated HCl, extract with two 100 ml aliquots of ethyl acetate to provide a brown oil product corresponding to 5-propyl-2-thiophenesulfonamide.

Analysis for $C_7H_{11}NO_2S_2$:
Theory: C, 40.96; H, 5.40; N, 6.82.
Found C, 41 18; H, 5.50; N, 6.59.

PMR 7 45 (d, J=6 Hz, 1H), 6.69 (d, J=6 Hz, 1H), 5.0 (s, 2H), 2.82 (m, 2H), 1.9 (m, 2H), 1 (t, J=6 Hz, 3H).

C. Preparation of 5-propyl-N-[[(4-chlorophenyl)amino]carbonyl]-2-thiophenesulfonamide sodium salt The procedure of Example 3B was followed with the sulfonamide from Example 15B (1.08 g, 5.3 mmole), acetone (6 ml), 1N NaOH (5.3 ml), and 4-chlorophenyl isocyanate (0.81 g, 5.3 mmole) to provide a gummy material. This was mixed with ethyl acetate to provide the product as a powder.

PMR (CD$_3$SOCD$_3$) 8.72 (s, 1H), 7.54 (d, J=9 Hz, 2H), 7.25 (d, J=4 Hz, 1H), 7.14 (d, J=9 Hz, 2H), 6.68 (d, J=4 Hz, 1H), 2.72 (t, J=8 Hz, 2H), 1.60 (sext, J=8 Hz, 2H) and 0.92 (t, J=8 Hz, 3H) ppm.

Analysis for C$_{14}$H$_{14}$ClN$_2$NaO$_3$S$_2$:
Theory: C, 44.15; H, 3.71; N, 7.36.
Found: C, 44.07; H, 3.63; N, 7.18.

EXAMPLE 16

Preparation of 3-ethyl-N-[[(4-chlorophenyl)amino]carbonyl]-2-thiophenesulfonamide The procedure of Example 3A was followed with 3-ethylthiophene (3.7 g, 33.5 mmole) in 20 ml of chloroform, chlorosulfonic acid (6.9 ml, 100 mmole), dry chloroform (110 ml) concentrated ammonium hydroxide, crystallization from toluene gave the 3-ethylthiophene2-sulfonamide product as white needles.

The process of Example 4B was followed with this sulfonamide (1.8 g, 9.4 mmole), acetone (10 ml), 1N NaOH (9.4 ml), 4-chlorophenyl isocyanate (1.44 g, 9.4 mmole), and concentrated HCl to give the name product as a white solid (2.61 g, 7.58 mmole).

PMR (CD$_3$SOCD$_3$) 10.66 (bs, 1H), 8.86 (s, 1H), 7.90 (d, J=6 Hz, 1H), 7.49 (d, J=9 Hz, 2H), 7.36 (d, J=9 Hz, 2H), 7.14 (d, J=6 Hz, 1H), 2.94 (q, J=9 Hz, 2H) and 1.10 (t, J=9 Hz, 3H) ppm.

Analysis for C$_{13}$H$_{13}$ClN$_2$O$_3$S$_2$:
Theory: C, 45.28; H, 3.80; N, 8.12.
Found: C, 45.45; H, 3.71; N, 8.02.

EXAMPLE 17

Preparation of N-[(3,4-dichlorophenyl)amino]carbonyl]-4,5-dimethyl-2-thiophenesulfonamide The procedure of Example 3A was followed with 2,3-dimethylthiophene (6.0 g, 53.6 mmole) in chloroform (40 ml), chlorosulfonic acid (27.5 g, 166 mmole) in chloroform (120 ml), concentrated ammonium hydroxide, water (200 ml), hexane (100 ml) to obtain the solid product of 4,5-dimethyl-2-thiophenesulfonamide.

Analysis for C$_6$H$_9$NO$_2$S$_2$:
Theory: C, 37.68; H, 4.74; N, 7.32.
Found: C, 37.94; H, 4.77; N, 7.07.

The procedure of Example 4B was followed with this dimethylthiophenesulfonamide (1.5 g, 7.7 mmole), 1N NaOH (7.7 ml), acetone (7 ml), 3,4-dichlorophenyl isocyanate (1.46 g, 7.7 mmole), 1N HCl (7.7 ml) to provide, after washing and extraction with ethyl ether and hexane and drying, the named product (2.25 g, 5.9 mmole).

PMR (CD$_3$SOCD$_3$) 9.18 (s, 1H), 7.80 (d, J=3 Hz, 1H), 7.50 (d, J=9 Hz, 1H) 7.46 (s, 1H), 7.34 (dd, J=3,9 Hz, 1H), 2.34 (s, 3H) and 2.10 (s, 3H) ppm Analysis for C$_{13}$H$_{12}$Cl$_2$N$_2$O$_3$S$_2$:
Theory: C, 41.17; H, 3.19; N, 7.39.
Found C, 40.92; H. 3.10; N, 7.30.

EXAMPLE 18

Preparation of N-[[(4-chlorophenyl)amino]carbonyl]-3-thiophenesulfonamide

A. Preparation of 3-thiophenesulfonamide

Equal volumes of 2,5-dibromothiophene and 27°-30% fuming sulfuric acid were added to a 100 ml round bottom flask immersed in an ice bath. The mixture was stirred for five minutes and then added to 200 ml of ice water. Sodium carbonate was added until carbon dioxide evolution ceased. The mixture was filtered and the aqueous filtrate stripped of solvent under vacuum. The resulting solid was combined with 300 ml of ethanol and the mixture heated to reflux for 2.5 hours. The hot solution was filtered. A solid formed which was washed with ethyl acetate and dried to provide sodium 2,5-dibromo-3-thiophenesulfonate. The sulfonate was added to 150 ml of water and about 40 gm of 5% sodium/mercury amalgam was added over a 0.5 hour period. The temperature was maintained at 35° C. or below The aqueous layer was decanted from the mercury and filtered. The filtrate was neutralized with 1N HCl to a pH of 7. The solution was then stripped to dryness. The resulting solid was heated to reflux in 200 ml of ethanol. The hot liquid was filtered and the filtrate condensed to provide an off-white solid of sodium 3-thiophenesulfonate. Phosphorous oxychloride (20 ml) was mixed with this thiophenesulfonate (3.17 g) and stirred at reflux for about two hours under a drying tube. The reaction mixture was cooled to room temperature and slowly added to ice. The resulting mixture was extracted with two 200-ml aliquots of a mixture of ethyl acetate and ethyl ether and the resulting organic layer extracted with water. The organic layer was isolated and the solvent removed under vacuum. The resulting residue was combined with 50 ml of concentrated ammonium hydroxide and stirred at room temperature. THF (50 ml) was added to obtain a homogenous mixture. After two hours of stirring, the mixture was partially concentrated and acidified with concentrated HCl. The resulting mixture was extracted with two 200-ml aliquots of a mixture of ethyl acetate and ethyl ether. The organic layers were combined and dried over sodium sulfate, filtered, and concentrated to provide a solid product. The solid was crystallized from ethyl acetate and dried to provide 3-thiophenesulfonamide (1.1 g).

B. Reaction of 3-thiophenesulfonamide and 4-chlorophenyl isocyanate

Procedure of Example 4B was followed with 3-thiophenesulfonamide (1.1 g, 6.81 mmole), acetone (10 ml), 1N NaOH (6.8 ml), 4-chlorophenyl isocyanate (1.05 g, 6.8 mmole) in acetone (10 ml), 1N HCl (8 ml) to give the N-[[(4-chlorophenyl)amino]carbonyl]-3-thiophenesulfonamide (1.44 g, 4 5 mmole).

PMR (CD$_3$SOCD$_3$) 8.96 (s, 1H), 8.18 (d, J=2 Hz, 1H), 7.64 (dd, J=2, 6 Hz, 1H), 7.48 (d, J=9 Hz, 2H), 7.44 (d, J=6 Hz, 1H) and 7.24 (d, J=9 Hz, 2H) ppm.

Analysis for C$_{11}$H$_9$ClN$_2$O$_3$S$_2$:
Theory: C, 41.71; H, 2.86; N, 8.84.
Found: C, 40.55; H, 2.72; N, 8.40.

EXAMPLE 19

Preparation of
N-[[(3,4-dichlorophenyl)amino]carbonyl]-5-ethyl-4-methyl-2-thiophenesulfonamide The procedure of Example 4B was followed with 5-ethyl-4-methyl-2-thiophenesulfonamide (1.5 g, 7.3 mmole), 3,4-dichlorophenyl isocyanate (1.38 g, 7.3 mmole), acetone (7 0 ml), 1H NaOH (7.3 ml), concentrated HCl to give the named product as a white solid (2.17 g, 5 2 mmole).

PMR (CD$_3$SOCD$_3$) 9.16 (s, 1H), 7 82 (d, J=3 Hz, 1H), 7.46 (d, J=9 Hz, 1H), 7.40 (s, 1H), 7.34 (dd, J=3, 9 Hz, 1H), 2.74 (q, J=9 Hz, 2H), 2.10 (s, 3H) and 1.18 (t, J=9 Hz, 3H) ppm.

Analysis for $C_{14}H_{14}Cl_2N_2O_3S_2$:
Theory: C, 42.75; H, 3.59; N, 7.13.
Found C, 42.65; H, 3.55; N, 7.43.

EXAMPLE 20

Preparation of
N-[[(3,4-dichlorophenyl)amino]carbonyl]-2-thiophenesulfonamide

2-Thiophenesulfonamide (1.55 g, 9.5 mmole) was combined with 3,4-dichlorophenyl isocyanate (1.79 g, 9.5 mmole), 1N NaOH (9.5 ml) and acetone (25 ml) followed by 1N HCl (9.5 ml) using the method of Example 4B to give the named product (1.3 g).

PMR (CD$_3$SOCD$_3$) 9.22 (s, 1H), 8.02 (dd, J=2,6 Hz, 1H), 7.82 (dd, J=2,6 Hz, 1H), 7.76 (d, J=3 Hz, 1H), 7.52 (d, J=9 Hz, 1H), 7.34 (dd, J=3,9 Hz, 1H) and 7.02 (dd, J=6,6 Hz, 1H) ppm.

Analysis for $C_{11}H_8Cl_2N_2O_3S_2$:
Theory: C, 37.62; H, 2.30; N, 7.98.
Found C, 37.85; H, 2.36; N, 7.97.

EXAMPLE 21

Preparation of
N-[[(4-chlorophenyl)amino]carbonyl]-5-ethyl-4-methyl-2-thiophenesulfonamide sodium salt 2-Acetyl-3-methylthiophene (15.0 g, 107 mmole) was contacted with hydrazine (15 ml), potassium hydroxide (75 g) in ethylene glycol (150 ml) using the method of Example 15A to provide 3-methyl-2-ethylthiophene (11.1 g). This thiophene (11.1 g, 88 mmole) was contacted with chlorosulfonic acid (18 ml, 270 mmole) using the method of Example 3A to provide 4-methyl-5-ethyl-2-thiophenesulfonamide.

Analysis for $C_7H_{11}NO_2S_2$:
Theory: C, 40.95; H, 5.40; N, 6.82.
Found : C, 41.12; H, 5.50; N, 6.81.

This thiophenesulfonamide (1.5 g, 7.3 mmole) was contacted with 4-chlorophenyl isocyanate (1.12 g, 7.3 mmole), 1N NaOH (7.3 ml) and acetone (6 ml) using the method of Example 3B to provide the named compound (1.2 g, 3.35 mmole).

PMR (CD$_3$SOCD$_3$) 8.70 (s, 1H), 7.72 (d, J=8 Hz, 2H), 7.16 (s, 1H), 7.14 (d, J=8 Hz, 2H), 2.68 (q, J=9 Hz, 2H), 2.04 (s, 3H) and 1.16 (t, J=9 Hz, 3H) ppm.

Analysis for $C_{14}H_{14}ClN_2NaO_3S_2$:
Theory: C, 44.15; H, 3 70; N, 7.35.
Found C, 44 20; H, 3.73; N, 7.28.

EXAMPLE 22

Preparation of
N-[[(4-chlorophenyl)amino]carbonyl]-2,5-dimethyl-3-thiophenesulfonamide The procedure of Example 4B was followed with 2,5-dimethyl-3-thiophenesulfonamide (1.73 g, 9.06 mmole), acetone (10 ml), 1N NaOH (9.1 ml), 4-chlorophenyl isocyanate (1.39 g, 9.0 mmole), 1N HCl (9.1 ml). The aqueous layer was extracted with two 100 ml aliquots of ethyl acetate, which were combined and washed with 50 ml of water. The organic layer was then dried over Na$_2$SO$_4$. The solvent was removed and the residue chromatographed using a mixture of 4% methanol/methylene chloride as the eluent over a 50 mm silica gel column. The solvent was removed to provide the named product.

m.s.=344 (M+).

Analysis for $C_{13}H_{13}ClN_2O_3S_2$:
Theory: C, 45.28; H, 3.80; N, 8.12.
Found C, 45.23; H, 3.75; N, 8.12.

EXAMPLE 23

Preparation of
N-[[(4-chlorophenyl)amino]carbonyl]-5-ethyl-2-pyrrolesulfonamide

4-Chloroaniline (4.5 g, 35.4 mmole) was combined with tetrahydrofuran (80 ml) under nitrogen and cooled to −78° C. Chlorosulfonyl isocyanate (3.0 ml, 35.4 mmole) was added and the mixture stirred 1 hour at −78° C. 2-Ethylpyrrole (3.66 g, 38.9 mmole) was added and the mixture allowed to warm to room temperature and then stirred for 2 hours. The reaction was quenched with water and then concentrated. The residue was dissolved in methylene chloride (100 ml) which was extracted with three 100 ml portions of aqueous NaOH. The aqueous layer was acidifed and extracted with methylene chloride. The organic layers were combined and washed with two 100 ml portions of water. The organic layer was then dried over Na$_2$SO$_4$, filtered and concentrated. The resulting dark oil was flashed chromatographed over silica eluding with 4% methanol/methylene chloride. Removal of solvent provided 0.64 g of product.

PMR (CD$_3$SOCD$_3$) 10.38 (s, 1H), 8.80 (s, 1H), 7 34 (d, J=9 Hz, 2H), 7.26 (d, J=9 Hz, 2H), 6.62 (d, J=3 Hz, 1H), 5.90 (d, J=3 Hz, 1H), 2.56 (q, J=9 Hz, 2H) and 1.12 (t, J=9 Hz, 3H) ppm. m.s. (FAB)=(M+) 328.

The compounds of formula I have been shown to be active against transplanted mouse tumors in vivo. The compounds were tested in C3H mice bearing a 6C3HED lymphosarcoma, also known as the Gardner lymphosarcoma (GLS). The 6C3HED lymphosarcoma was obtained from the Division of Cancer Treatment, National Cancer Institute, Tumor Bank, maintained at E. G. and G. Mason Research (Worcester, Mass.). First passage tumor was stored in liquid nitrogen using standard techniques. The transplanted tumor was reestablished from the Tumor Bank every six months or as needed. The tumor was maintained by serial passage twice weekly in C3H mice.

In the procedure the tumor was removed from passage animals and minced into 1- to 3-mm square fragments using sterile techniques. Tumor pieces were checked for sterility using both Antibiotic Medium 1 and Brain Heart Infusion (Difco, Detroit, Mich.). Recipient mice were shaved and tumor pieces were implanted subcutaneously in the auxiliary region by trocar. Drug therapy on the appropriate schedule was initiated on the day after tumor implant. The compound being tested was mixed with 2.5% Emulphor EL620 from GAF Corporation (1:40 dilution in saline). All animals were weighed at the beginning and end of administration of the subject compounds. Food and water were provided ad libitum. The drug was administered orally in 0.5 ml of 2.5% Emulphor (unless otherwise indicated). The tumor was measured the day after treatment ended with two dimensional measurements (width and length) of the tumor taken using Vernier calipers. Tumor weights were calculated from these measurements using the following formula:

Tumor weight (mg) = [tumor length (mm) × tumor width (mm)]$^2$ ÷ 2

At least one control group of an equal number of mice was treated with the same volume of 2.5% Emulphor only. The percent inhibition is determined by subtracting the ratio of the mean tumor size of the test group relative to the control group from one and multiplying the result times 100.

The results of several experiments in mice bearing a 6C3HED lymphosarcoma when the instant compounds were administered orally are provided in Table I. In the Table, column 1 gives the example number of the compound, column 2 lists the dose level, column 3 provides the percent inhibition of tumor growth, and column 4 gives the number of mice which died relative to the total number of animals in the group.

TABLE I

| Example No. | Dose[1] | Percent Inhibition[2] | Toxic/Total[3] |
|---|---|---|---|
| 1 | 300.0 | 80 | 0/10 |
|  | 150.0 | 57 | 0/10 |
| 2 | 300.0 | 96 | 0/10 |
|  | 150.0 | 69 | 0/10 |
| 3 | 300.0[4] | 89 | 0/7 |
|  | 150.0[4] | 57 | 0/7 |
| 4 | 300.0 | 100 | 4/10 |
|  | 150.0 | 6 | 1/10 |
| 5 | 1200.0 | — | 10/10 |
|  | 600.0 | — | 10/10 |
|  | 300.0 | 100 | 0/10 |
|  | 150.0 | 93 | 0/10 |
|  | 75.0 | 50 | 0/10 |
|  | 37.5 | 21 | 0/10 |
| 6 | 300.0 | 66 | 3/10 |
|  | 150.0 | 16 | 0/10 |
| 7 | 300.0 | 61 | 1/10 |
|  | 150.0 | 24 | 0/10 |
| 8 | 300.0[4] | 62 | 1/10 |
|  | 150.0[4] | 29 | 0/10 |
| 9 | 300.0 | 63 | 0/10 |
|  | 150.0 | 57 | 0/10 |
| 10 | 300.0[4] | 63 | 0/10 |
|  | 150.0[4] | 44 | 0/10 |
| 11 | 300.0 | 100 | 2/10 |
|  | 150.0 | 57 | 0/10 |
| 12 | 300.0 | 62 | 1/10 |
|  | 150.0 | 17 | 0/10 |
| 13 | 300.0 | 52 | 0/10 |
|  | 150.0 | 25 | 0/10 |
| 14 | 300.0 | 73 | 0/10 |
|  | 150.0 | 42 | 0/10 |
| 15 | 300.0[4] | 15 | 1/10 |
|  | 150.0[4] | 41 | 0/10 |
| 16 | 300.0[4] | 25 | 0/10 |
|  | 150.0[4] | 21 | 0/10 |
| 17 | 300.0 | 69 | 0/10 |
|  | 150.0 | 30 | 0/10 |
| 18 | 300.0 | — | 10/10 |
|  | 150.0 | 27 | 0/10 |
| 19 | 300.0 | 42 | 1/10 |
|  | 150.0 | 17 | 0/10 |
| 20 | 300.0 | 64 | 4/10 |
|  | 150.0 | 36 | 0/10 |
| 21 | 300.0 | 58 | 0/10 |
|  | 150.0 | 26 | 0/10 |
| 22 | 300.0 | 38 | 0/10 |
|  | 150.0 | 9 | 1/10 |
| 23 | 300.0 | 56 | 0/10 |

[1] Amount of compound used for each dose in milligrams per kilogram of body weight
[2] [1-(Mean tumor weight in test group/mean tumor weight in control group)] × 100
[3] Number of mice which died during test period/total number of mice in test group.
[4] Compound administered orally in 0.6 ml of Emulphor.

The compounds of Formula I are antineoplastic agents and the invention provides a method of treating susceptible neoplasms. In particular the present compounds are useful in treating solid tumors including carcinomas such as ovarian, non-small cell lung, gastric pancreatic, prostate, renal cell, breast, colorectal, small cell lung, melanoma and head and neck; and sarcomas such as Kaposi's sarcoma and rhabdomyosarcoma.

The instant compounds can be administered individually or in combination, preferably orally, and usually in the form of a pharmaceutical composition. Such compositions are prepared in a manner well known in the pharmaceutical art and comprise at least one active compound. Accordingly, the present invention also includes pharmaceutical compositions comprising as active ingredient certain compounds of Formula I associated with a pharmaceutically acceptable carrier, and the invention further comprises the method of treating susceptible neoplasms using the compositions containing as an active ingredient a compound of Formula I.

In making the compositions of the present invention, as well as compositions containing other compounds of Formula I, the active ingredients are usually mixed with an excipient, diluted by an excipient or enclosed within such a carrier which can be in the form of a capsule, sachet, paper or other container. When the excipient serves as a diluent, it can be a solid, semi-solid or liquid material which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

In preparing a formulation it may be necessary to mill the active compound to provide the appropriate particle size prior to combining with the other ingredients. If the active compound is substantially insoluble, it ordinarily is milled to a particle size of less than about 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include lubricating agents such as talc, magnesium stearate and mineral oil, wetting agents, emulsifying and suspending agents, preserving agents such as methyl- and propylhydroxybenzoates, sweetening agents or flavoring agents. The compositions of the invention can be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are effective over a wide dosage range. For example, dosages per day normally fall within the range of about 0.5 to about 1200 mg/kg of body weight. In the treatment of adult humans, the range of about 1 to about 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following formulation examples can employ as active compounds any of the compound of Formula I. The examples are illustrative only and are not intended to limit the scope of the invention in any way.

FORMULATION 1

Hard gelatin capsules are prepared using the following ingredients:

|  | Quantity (mg/capsule) |
| --- | --- |
| N-[[(4-chlorophenyl)amino]-carbonyl]-5-methoxy-2-thiophenesulfonamide | 250 |
| Starch | 305 |
| Magnesium stearate | 5 |

The above ingredients are mixed and filled into hard gelatin capsules in 560 mg quantities.

FORMULATION 2

A tablet formula is prepared using the ingredients below:

|  | Quantity (mg/tablet) |
| --- | --- |
| 5-Ethoxy-N-[[(4-chlorophenyl)-amino]carbonyl]-2-thiophenesulfonamide | 250 |
| Cellulose, microcrystalline | 400 |
| Colloidal Silicon dioxide | 10 |
| Stearic acid | 5 |

The components are blended and compressed to form tablets each weighing 665 mg.

FORMULATION 3

A dry powder inhaler formulation is prepared containing the following components:

|  | Weight % |
| --- | --- |
| 5-Ethoxy-N-[[(4-chlorophenyl)-amino[carbonyl]-2-thiopheneformamide | 5 |
| Lactose | 95 |

The active compound is mixed with the lactose and the mixture added to a dry powder inhaling appliance.

FORMULATION 4

Tablets each containing 60 mg of active ingredient are made up as follows:

| N-[[(4-chlorophenyl)amino-carbonyl]-5-ethyl-2-furan-sulfonamide | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 20 mesh U.S. sieve and mixed thoroughly. The solution of polyvinylpyrrolidone is mixed with the resultant powders which are then passed through a No. 4 mesh U.S. sieve. The granules so produced are dried at 50°–60° C. and passed through a No. 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 150 mg.

FORMULATION 5

Capsules each containing 80 mg of medicament are made as follows:

| 5-Chloro-N-[[(4-chlorophenyl)-amino]carbonyl]-2-thiophenesulfonamide | 80 mg |
| --- | --- |
| Starch | 109 mg |
| Magnesium stearate | 1 mg |
| Total | 190 mg |

The active ingredient, cellulose, starch and magnesium stearate are blended, passed through a No. 20 mesh U.S. sieve, and filled into hard gelatin capsules in 190 mg quantities.

FORMULATION 6

Suppositories each containing 225 mg of active ingredient are made as follows:

| N-[[(4-Chlorophenyl)amino]-carbonyl]-5-ethyl-2-thiophenesulfonamide sodium salt | 225 mg |
| --- | --- |
| Saturated fatty acid | 2,000 mg |

-continued

| | |
|---|---|
| glycerides to | |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per 5 ml dose are made as follows:

| | |
|---|---|
| N-[(4-chlorophenyl)amino]-carbonyl]-4,5-dimethyl-2-thiophenesulfonamide | 50 mg |
| Xanthan Gum | 4 mg |
| Sodium carboxymethyl cellulose (11%) | 50 mg |
| Microcrystalline Cellulose (89%) | |
| Sucrose | 1.75 g |
| Sodium Benzoate | 10 mg |
| Flavor | q.v. |
| Color | q.v. |
| Purified water to | 5 ml |

The medicament, sucrose and xanthan gum are blended, passed through a No. 10 mesh U.S. sieve, and then mixed with a previously made solution of the microcrystalline cellulose and sodium carboxymethylcellulose in water. The sodium benzoate, flavor and color are diluted with some of the water and added with stirring. Sufficient water is then added to produce the required volume

FORMULATION 8

Capsules each containing 150 mg of medicament are made as follows:

| | |
|---|---|
| N-[[(4-chlorophenyl-)amino]-carbonyl]-5-methoxy-2-thiophenesulfonamide | 150 mg |
| Starch | 407 mg |
| Magnesium stearate | 3 mg |
| Total | 560 mg |

The active ingredient, cellulose, starch and magnesium stearate are blended, passed through a No. 20 mesh U.S. sieve, and filled into hard gelatin capsules in 560 mg quantities.

What is claimed is:

1. A compound of Formula I $$A-SO_2-NH-\overset{O}{\underset{\|}{C}}-NH-\underset{X^2}{\overset{X^1}{\bigcirc}}\qquad I$$

wherein $X^1$ and $X^2$ are independently hydrogen, halo, methyl or trifluoromethyl with the proviso that at least one of $X^1$ and $X^2$ is chlorine, bromine, fluorine or trifluoromethyl;

A is $$\underset{Z}{\overset{R^2\quad R^3}{\bigcirc}}-\xi\quad\text{or}\quad\underset{Z}{\overset{R^2}{\bigcirc}}-R^4$$

wherein:

Z is sulfur, oxygen or nitrogen;

$R^1$, $R^2$, $R^3$, and $R^4$ are independently hydrogen, halo, $C_1$-$C_3$ alkyl, $C_1$-$C_3$ alkoxy, or $C_1$-$C_3$ alkylthio with the proviso that when A is $$\underset{Z}{\overset{R^2\quad R^3}{\bigcirc}}-\xi$$

at least one of $R^1$, $R^2$, or $R^3$, is a substituent other than hydrogen, and pharmaceutically acceptable salts thereof.

2. A compound of claim 1 wherein Z is oxygen or sulfur.

3. A compound of claim 2 wherein $X^1$ and $X^2$ are independently chlorine, bromo, fluorine, trifluoromethyl or hydrogen with the proviso that at least one of $X^1$ and $X^2$ is chlorine or bromine and $R^1$, $R^2$, $R^3$ and $R^4$ are independently hydrogen, $C_1$-$C_2$ alkyl, $C_1$-$C_2$ alkoxy, $C_1$-$C_2$ alkylthio, chlorine or bromine.

4. A compound of claim 1 selected from the group consisting of N-[[(4-chlorophenyl)amino]carbonyl]-4,5-dimethyl-2-thiophenesulfonamide; N-[[(3,4-dichlorophenyl)amino]carbonyl]-4,5-dimethyl-2-thiophenesulfonamide; N-[[(4-chlorophenyl)amino]carbonyl]-5-(methylthio)-2-thiophenesulfonamide; N-[[(3,4-dichlorophenyl)amino]carbonyl]-5-methyl-2-thiophenesulfonamide; N-[[(4-chlorophenyl)amino]carbonyl]-5-propoxy-2-thiophenesulfonamide; N-[[(3,4-dichlorophenyl)amino]carbonyl]-5-ethyl-2-thiophenesulfonamide; N-[[(4-dichlorophenyl)amino]carbonyl]-3-methyl-2-thiophenesulfonamide; N-[[(4-chlorophenyl)amino]carbonyl]-5-chloro-2-thiophenesulfonamide; N-[[(4-chlorophenyl)amino]carbonyl]-5-ethyl-2-thiophenesulfonamide; N-[[(4-chlorophenyl)amino]carbonyl]-5-ethyl-2-furansulfonamide; N-[[(4-chlorophenyl)amino]carbonyl]-5-methoxyl-2-thiophenesulfonamide; N-[[(4-chlorophenyl)amino]carbonyl]-5-methyl-2-thiophenesulfonamide; N-[[(4-chlorophenyl)amino]carbonyl]-5-ethoxy-2-thiophenesulfonamide and the salts thereof.

5. A compound of claim 4 selected from the group consisting of N-[[(4-chlorophenyl)amino]carbonyl]-5-chloro-2-thiophenesulfonamide; N-[[(4-chlorophenyl)amino]carbonyl]-5-ethyl-2-thiophenesulfonamide; N-[[(4-chlorophenyl)amino]carbonyl]-5-ethyl-2-furansulfonamide; N-[[(4-chlorophenyl)amino]carbonyl]-5-methoxy-2-thiophenesulfonamide; N-[[(4-chlorophenyl)amino]carbonyl]-5-ethoxy-2-thiophenesulfonamide and the salts thereof.

6. A compound of claim 5 which is N-[[(4-chlorophenyl)amino]carbonyl]-5-methoxy-2-thiophenesulfonamide.

* * * * *

UNITED STATES PATENT AND TRADEMARK OFFICE
CERTIFICATE OF CORRECTION

PATENT NO.   : 5,302,724
DATED        : April 12, 1994
INVENTOR(S)  : Howbert, et al Page 1 of 6

It is certified that error appears in the above-indentified patent and that said Letters Patent is hereby corrected as shown below:

On the cover page, item [56] reads "U.S. Patent Document 4,471,757 5/1978 Levitt" and should read "U.S. Patent Document 4,471,757 5/1988 Levitt".

In column 2, line 46 reads "$R^1$, $R^2$, $R^3$, and $R^4$ are independently hydrogen," and should read "$R^1$, $R^2$, $R^3$ and $R^4$ are independently hydrogen, halo,"

In column 4, line 51 reads "$X^1$, $X^2$, Z, $R^1$, $R^2$, $R^3$, and $R^4$ are the same as previously defined." and should read "where $X^1$, $X^2$, Z, $R^1$, $R^2$, $R^3$, and $R^4$ are the same as previously defined."

In column 6, line 55 reads "2H), 7.40(d, J=6 Hz, 1H), 7.28 (d, J=9 Hz, 2H), 6 36" and should read "2H), 7.40(d, J=6 Hz, 1H), 7.28 (d, J=9 Hz, 2H), 6.36"

In column 6, line 58 reads "Analysis for $C_{13}H_{13}ClN_2O_4S_2$:" and should read "Analysis for $C_{13}H_{13}C_1N_2O_4S_2$:"

In column 6, line 68 reads "pleted, the reaction was stirred at 0° C. for 30 min The" and should read "pleted, the reaction was stirred at 0° C. for 30 min. The"

In column 7, line 12 reads "washed with water, dried (sodium sulfate)" and filtered" and should read "washed with water, dried (sodium sulfate) and filtered."

In column 7, line 46 reads "Found C, 43.36; H, 3.37; N, 7.52." and should read "Found: C, 43.36; H, 3.37; N, 7.52."

In column 7, line 62 reads "To a solution of 5-chloro-2-thiophenesulfonamide 1.9" and should read "To a solution of 5-chloro-2-thiophenesulfonamide (1.9"

UNITED STATES PATENT AND TRADEMARK OFFICE
CERTIFICATE OF CORRECTION

PATENT NO. : 5,302,724
DATED : April 12, 1994
INVENTOR(S) : Howbert, et al

It is certified that error appears in the above-indentified patent and that said Letters Patent is hereby corrected as shown below:

In column 7, line 64 reads "sodium hydroxide (10 ml of 1N 10 mmole) followed by" and should read "sodium hydroxide (10 ml of 1N, 10 mmole) followed by"

In column 8, line 24 reads "under vacuum. To the resuling residue was added a" and should read "under vacuum. To the resulting residue was added a"

In column 8, line 32 reads "ride The combined organic phases were washed with" and should read "ride. The combined organic phases were washed with"

In column 8, line 51 reads "washed with water The material was slurried with a" and should read "washed with water. The material was slurried with a"

In column 9, line 5 reads "g of named product were obtained" and should read "g of named product were obtained."

In column 9, line 31 reads "Theory: C, 37 22; H, 2.34; N, 7.23." and should read "Theory: C, 37.22; H, 2.34; N, 7.23."

In column 10, line 25 reads "(9.5 ml, 15.2 mmole) and $SO_2$ gas for 15 minutes Sodium" and should read "(9.5 ml, 15.2 mmole) and $SO_2$ gas for 15 minutes. Sodium"

In column 12, line 4 reads "Theory: C, 27.84; H, 1.49; N, 5.9." and should read "Theory: C, 27.84; H, 1.49; N, 5.90."

In column 12, line 65 reads "Found C, 41 18; H, 5.50; N, 6.59." and should read "Found: C, 41.18; H, 5.50; N, 6.59."

UNITED STATES PATENT AND TRADEMARK OFFICE
CERTIFICATE OF CORRECTION

PATENT NO. : 5,302,724
DATED : April 12, 1994
INVENTOR(S) : Howbert, et al

Page 3 of 6

It is certified that error appears in the above-indentified patent and that said Letters Patent is hereby corrected as shown below:

In column 12, line 66 reads "PMR 7 45 (d,J=6Hz,1H),6.69(d,J=6Hz,1H0,5.0)" and should read "PMR 7.45 (d,J=6Hz,1H),6.69(d,J=6Hz,1H0,5.0)"

In column 13, line 28 reads "phene2-sulfonamide product as white needles." and should read "phene-2-sulfonamide product as white needles."

In column 13, line 45 reads "N-[(3,4-dichlorophenyl)amino]carbonyl]-4,5-dimethyl-" and should read "N-[[(3,4-dichlorophenyl)amino]carbonyl]-4,5-dimethyl-"

In column 14, line 9 reads "27°-30% fuming sulfuric acid were added to a 100 ml" and should read "27-30% fuming sulfuric acid were added to a 100 ml"

In column 14, line 24 reads "or below The aqueous layer was decanted from the" and should read "or below. The aqueous layer was decanted from the"

In column 14, line 61 reads "fonamide (1.44 g, 4 5 mmole)." and should read "fonamide (1.44 g, 4.5 mmole)."

In column 15, line 10 reads "mmole),acetone(7 0ml), 1H NaOH (7.3ml), concen-" and should read ""mmole),acetone(7.0ml), 1H NaOH (7.3ml), concen-"

In column 15, line 12 reads "(2.17g, 5 2 mmole)." and should read "(2.17g, 5.2 mmole)."

In column 15, line 13 reads "PMR ($CD_3SOCD_3$) 9.16 (s, 1H), 7 82 (d, J=3 Hz," and should read "PMR ($CD_3SOCD_3$) 9.16 (s, 1H), 7.82 (d, J=3 Hz,"

In column 15, line 20 reads "Found C, 42.65; H, 3.55; N, 7.43," and should read "Found: C, 42.65; H, 3.55; N, 7.43,"

UNITED STATES PATENT AND TRADEMARK OFFICE
CERTIFICATE OF CORRECTION

PATENT NO. : 5,302,724
DATED : April 12, 1994
INVENTOR(S) : Howbert, et al

Page 4 of 6

It is certified that error appears in the above-indentified patent and that said Letters Patent is hereby corrected as shown below:

In column 15, line 38 reads "Found C, 37.85; H, 2.36; N,7.97," and should read "Found: C, 37.85; H, 2.36; N, 7.97,"

In column 15, line 66 reads "Theory: C, 44.15; H, 3 70; N, 7.35." and should read "Theory: C, 44.15; H, 3.70; N, 7.35."

In column 15, line 67 reads "Found C, 44 20; H, 3.73; N, 7.28." and should read "Found: C, 44.20; H, 3.73; N, 7.28."

In column 16, line 21 reads "Found C, 45.23; H, 3.75; N, 8.12." and should read "Found: C, 45.23; H, 3.75; N, 8.12."

In column 16, line 46 reads "PMR (CD3SOCD3) 10.38 (s, 1H), 8.80 (s,1H), 7 34" and should read "PMR (CD3SOCD3) 10.38 (s,1H), 8.80 (s, 1H), 7.34"

In column 21, line 16 reads "N-[(4-chlorophenyl)amino]-    50 mg" and should read "N-[[(4-chlorophenyl)amino]-    50 mg"

In column 21, line 41 reads "N-[[(4-chlorophenyl-)amino]-    150 mg" and should read "N-[[(4-chlorophenyl)amino]-    150 mg"

In column 22, line 27 reads "independently chlorine, bromo, fluorine, trifluoro-" and should read "independently chlorine, bromine, fluorine, trifluoro-"

UNITED STATES PATENT AND TRADEMARK OFFICE
CERTIFICATE OF CORRECTION

PATENT NO. : 5,302,724
DATED : April 12, 1994
INVENTOR(S) : Howbert, et al

It is certified that error appears in the above-indentified patent and that said Letters Patent is hereby corrected as shown below:

Column 22, lines 38-42, should read as follows:

4. A compound of Claim 1 selected from the group consisting of N-[[(4-chlorophenyl)amino]carbonyl]-4,5-dimethyl-2-thiophenesulfonamide; N-[[(3,4-dichlorophenyl)amino]carbonyl]-4,5-dimethyl-2-thiophenesulfonamide; N-[[(4-chlorophenyl)amino]carbonyl]-5-(methylthio)-2-thiophenesulfonamide; N-[[(3,4-dichlorophenyl)amino]carbonyl]-2-thiophenesulfonamide; N-[[(3,4-dichlorophenyl)amino]carbonyl]-5-methyl-2-thiophenesulfonamide; N-[[(4-chlorophenyl)amino]carbonyl]-5-propoxy-2-thiophensulfonamide; N-[[(3,4-dichlorophenyl)amino]carbonyl]-5-ethyl-2-thiophenesulfonamide; N-[[(4-chlorophenyl)amino]carbonyl]-3-methyl-2-thiophenesulfonamide; N-[[(4-chlorophenyl)amino]carbonyl]-5-

UNITED STATES PATENT AND TRADEMARK OFFICE
CERTIFICATE OF CORRECTION

PATENT NO. : 5,302,724
DATED : April 12, 1994
INVENTOR(S) : Howbert, et al

It is certified that error appears in the above-indentified patent and that said Letters Patent is hereby corrected as shown below:

chloro-2-thiophenesulfonamide; N-[[(4-chlorophenyl)-amino]carbonyl]-5-ethyl-2-thiophenesulfonamide; N-[[(4-chlorophenyl)amino]carbonyl]-5-ethyl-2-furansulfonamide N-[[(4-chlorophenyl)amino]carbonyl]-5-methoxy-2-thiophenesulfonamide; N-[[(4-chlorophenyl)amino]carbonyl]-5-methyl-2-thiophenesulfonamide; N-[[(4-chlorophenyl)-amino]carbonyl]-5-ethoxy-2-thiophenesulfonamide and the salts thereof.

Signed and Sealed this

Seventeenth Day of September, 1996

BRUCE LEHMAN

*Attest:*

*Attesting Officer*     *Commissioner of Patents and Trademarks*